United States Patent [19]

Lemrow

[11] Patent Number: Plant 6,706

[45] Date of Patent: Mar. 28, 1989

[54] WHITE CLIMBING MINIATURE ROSE NAMED LEMFALL

[75] Inventor: Maynard Lemrow, Spring Valley, Calif.

[73] Assignee: Nor'East Miniature Roses, Inc., Rowley, Mass.

[21] Appl. No.: 117,078

[22] Filed: Nov. 5, 1987

[51] Int. Cl.[4] ..... A01H 5/00

[52] U.S. Cl. ..... Plt./3

[58] Field of Search ..... Plt./3

*Primary Examiner*—Robert E. Bagwill

*Attorney, Agent, or Firm*—Vincent G. Gioia

[57] ABSTRACT

A new white climbing miniature rose.

2 Drawing Sheets

The present invention relates to a new and distinct variety of rose plant of the climbing miniature rose class, which was originated by my crossing as seed parent the variety known as "Jeanne Lajoie" and as polley parent an unnamed, unpatented seedling of my creation. The denomination of this new rose is "Lemfall".

Among the novel characteristics possessed by this new variety which distinguish it from its parents and all other varieties of which I am aware are its climbing growth habit and attractive many petaled white blooms which are semi-spherical pompon shaped when fully open. Asexual reproduction by budding of the new variety as performed in San Bernardino County, Calif., shows that the foregoing and other distinguishing characteristics come true to form and are established and transmitted through succeeding propagations.

The accompanying drawings show typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "157A" is plate 157A of The Royal Horticultural Society Colour Chart.

Parentage: Seedling.

*Seed parent.*—"Jeanne Lajoie".

*Pollen parent.*—Unnamed seedling.

Class: Climbing Miniature.

The following observations are made of specimens grown outdoors in San Bernardino County, Calif., during the month of August.

FLOWER

Blooming habit: Recurrent.

A. Bud:

(1) *Size.*—Medium.

(2) *Form.*—Ovoid, recessed center.

(3) *Color.*—As sepals divide, bud color is near 157A.

(4) *Sepals.*—Longer than bud, reddish tips, few appendages.

(5) *Peduncle.*—Length — about 1¼ to 1½ inches. Aspect — straight and curved. Strength — erect. Color — near 144A.

B. Bloom:

(1) *Size.*—Average size when fully expanded — about 1½ inches.

(2) *Borne.*—Several together in sprays.

(3) *Form.*—Ovoid buds with recessed centers open into flat blooms; petals quill to points and roll under retaining recessed center until fully open then becoming semi-spherical, pompon shaped.

(4) *Petalage.*—Number of petals under normal conditions — about 40 to 50.

(5) *Color.*—Petal undersurface of buds tends to near greenish white 157D to 157A with recessed center with bunched petals appearing near 158D. As petals unfurl, petal top surface appears near 155D to 155B but greenish white cast remains on petal undersurface most visible through ½ open stage. Thereafter, as flowers mature and age, color whitens still further. Petals drop easily on spent blooms very quickly.

C. Petals:

(1) *Texture.*—Average.

(2) *Appearance.*—Inside satiny and outside satiny.

(3) *Form.*—Broad, fan shaped with pointed apices.

(4) *Arrangement.*—Regularly arranged.

(5) *Petaloids in center.*—Many.

(6) *Persistence.*—Drop off cleanly and quickly.

(7) *Fragrance.*—Slight.

(8) *Lasting quality.*—Average.

REPRODUCTIVE ORGANS

A. Stamens, filaments and anthers:

*Arrangement and color.*—Regularly arranged around styles. Color — white anthers, pale green filaments.

B. Pollen:

*Color.*—Near white.

C. Styles: Bunched, medium length.

D. Stigmas:

*Color.*—Near pale green.

E. Hips: None observed.

PLANT

A. Form: Spreading plant with long canes typical of climbing miniature habit terminating in apical flower sprays similar to pillar-type roses.

B. Growth: Vigorous, uniform branching.

*Height attained.*—About 1½ to 2 feet.

C. Foliage: Compound 5 leaflets.

(1) *Size.*—Average for large flowered miniatures.

(2) *Quantity.*—Average.

(3) *Color.*—New foliage: green with reddish cast. Old foliage: Upper side — near 137A. Under side — near to 139C.

(4) *Shape.*—Oval, pointed.

(5) *Texture.*—Upper side is semiglossy; under side is matte.

(6) *Edge.*—Serrate.

(7) *Serration.*—Ordinary.

(8) *Leaf stem.*—Color — near to 137C. Under side — near 138C.

(9) *Stipules.*—Medium length, narrow, slightly bearded.

(10) *Resistance to disease.*—Blackspot — Average. Mildew — Average. Rust — Average.

D. Wood:

(1) *New wood.*—Color — pale green. Bark — smooth.

(2) *Old wood.*—Color — near 138A. Bark — smooth.

E. Thorns:

(1) *Thorns.*—Quantity (main stalk) — ordinary. On laterals from stalk — average. Form — flat base, straight, pointed. Length — medium. Color — pink base, tan points. Position — irregular.

F. Winter hardiness: Needs protection in severe climates.

I claim:

1. A new and distinct variety of rose plant of the climbing miniature rose class and all parts thereof, substantially as shown and described, characterized particularly by a climbing habit of growth and attractive many petaled white semi-spherical pompon shaped fully open flowers.

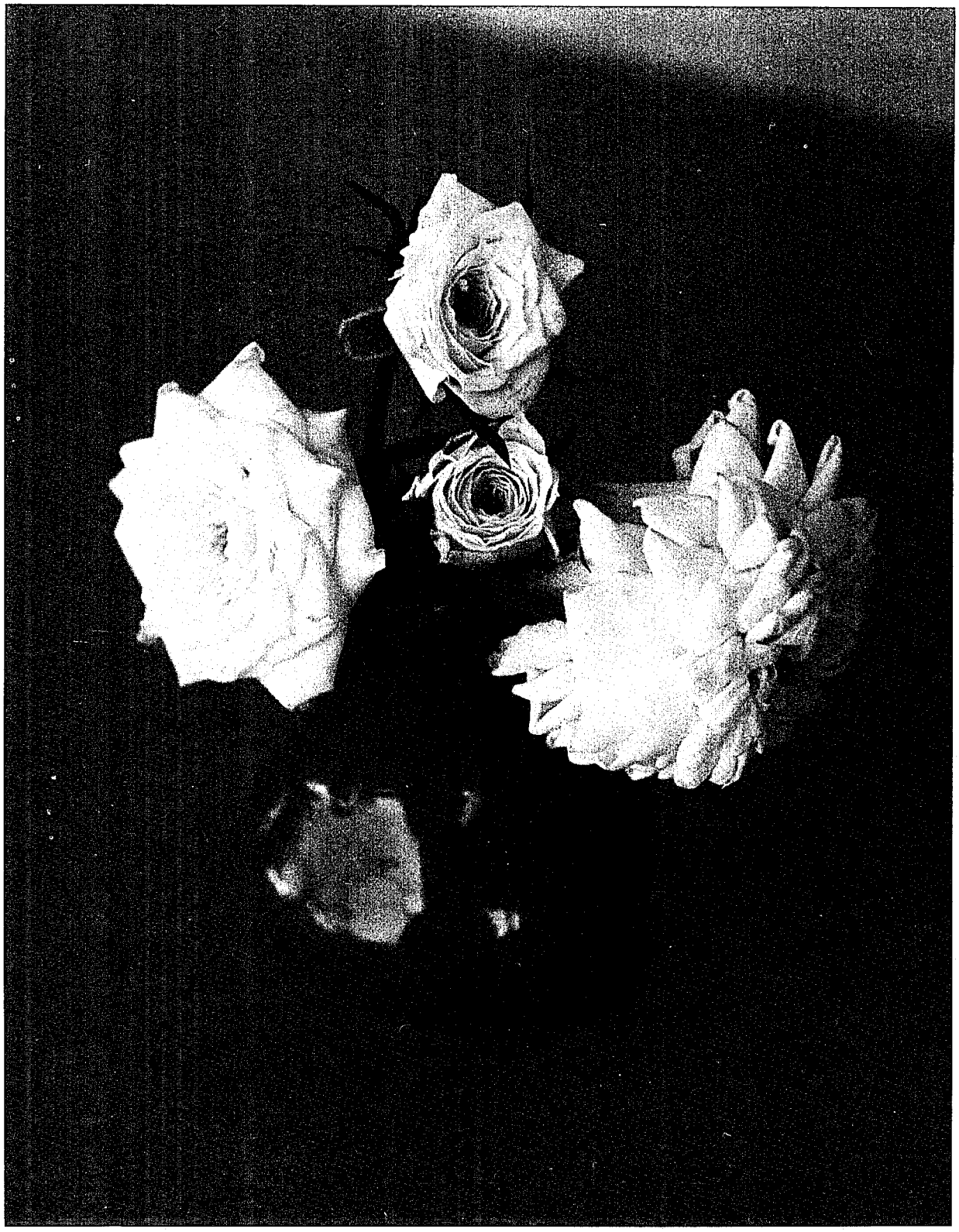

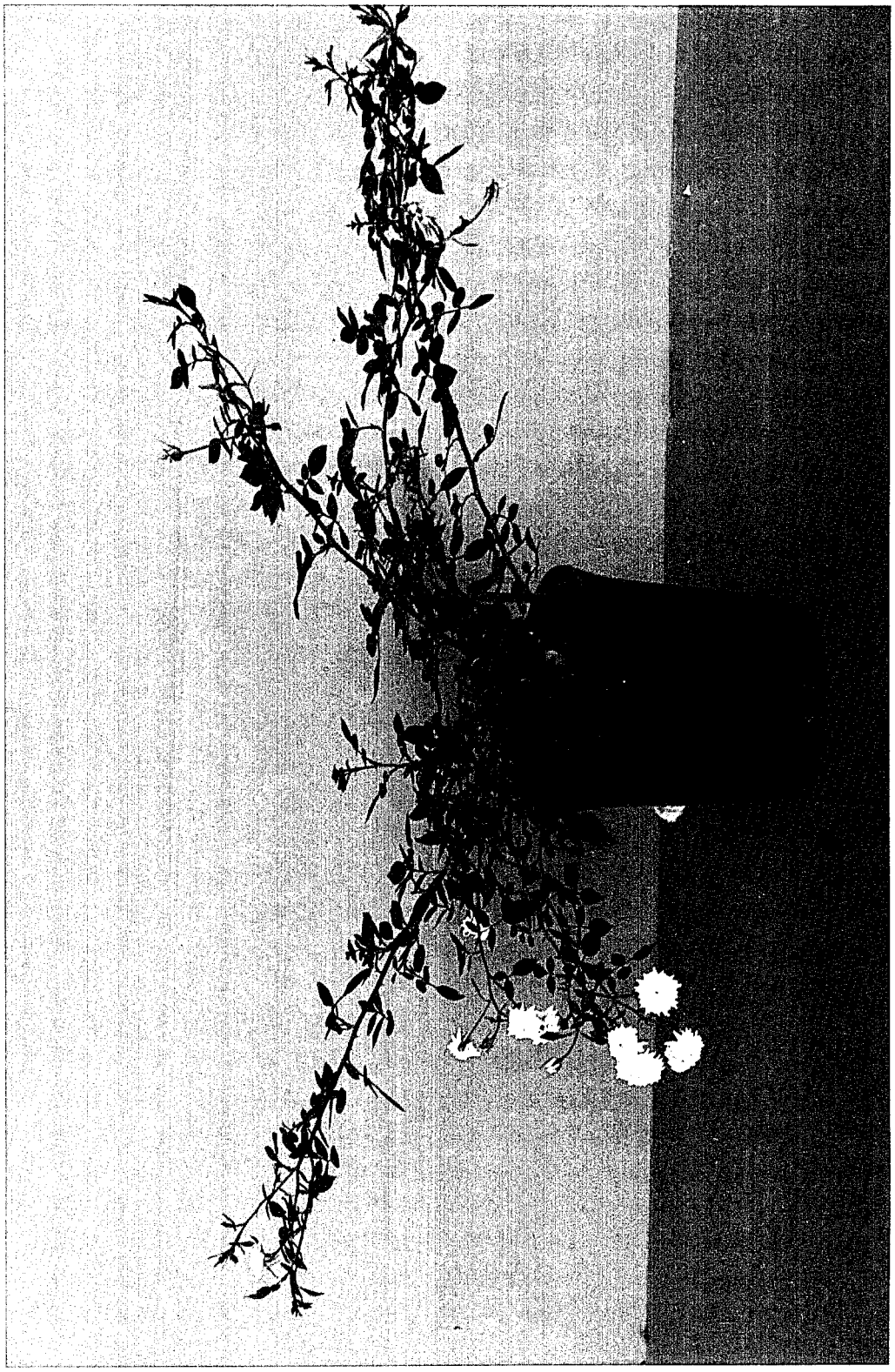

* * * * *